(12) United States Patent
Sinofsky et al.

(10) Patent No.: US 6,796,972 B1
(45) Date of Patent: Sep. 28, 2004

(54) CATHETER ANCHORING BALLOON STRUCTURE WITH IRRIGATION

(75) Inventors: Edward L. Sinofsky, Dennis, MA (US); Lincoln S. Baxter, Centerville, MA (US); Brian MacLean, Newton, MA (US)

(73) Assignee: Edwards Lifesciences LLC, Irvine, CA (US)

( * ) Notice: Subject to any disclaimer, the term of this patent is extended or adjusted under 35 U.S.C. 154(b) by 185 days.

(21) Appl. No.: 09/616,303

(22) Filed: Jul. 14, 2000

(51) Int. Cl.[7] .................................................. A61M 25/00
(52) U.S. Cl. .................... 604/264; 604/236; 604/164.1; 604/93.01; 604/96.01
(58) Field of Search .................... 604/93.01, 96.01, 604/164.1, 523, 544; 606/191

(56) References Cited

U.S. PATENT DOCUMENTS

| | | | |
|---|---|---|---|
| 4,625,724 A | | 12/1986 | Suzuki et al. ............ 128/303.1 |
| 4,701,166 A | | 10/1987 | Groshong et al. .......... 604/247 |
| 4,718,417 A | | 1/1988 | Kittrell et al. ........... 128/303.1 |
| 4,777,951 A | * | 10/1988 | Cribier et al. .............. 606/194 |
| 4,878,725 A | | 11/1989 | Hessel et al. ............. 350/96.15 |
| 4,929,246 A | * | 5/1990 | Sinofsky ........................ 606/8 |
| 4,986,830 A | * | 1/1991 | Owens et al. ............... 606/194 |
| 5,078,681 A | | 1/1992 | Kawashima ................. 604/53 |
| 5,125,925 A | | 6/1992 | Lundahl ...................... 606/15 |
| 5,242,398 A | | 9/1993 | Knoll et al. ................. 604/101 |
| 5,242,438 A | | 9/1993 | Saadatmanesh et al. ...... 606/15 |
| 5,261,904 A | | 11/1993 | Baker et al. .................. 606/17 |
| 5,350,375 A | | 9/1994 | Deckelbaum et al. .......... 606/7 |
| 5,429,483 A | * | 7/1995 | Tamari ........................ 417/307 |
| 5,575,772 A | | 11/1996 | Lennox ........................ 604/96 |
| 5,591,129 A | * | 1/1997 | Shoup et al. ............. 604/103.1 |
| 5,653,734 A | | 8/1997 | Alt .................................. 607/5 |
| 5,716,373 A | | 2/1998 | Wolvek et al. .............. 606/194 |
| 5,779,670 A | | 7/1998 | Bidwell et al. ............. 604/172 |
| 5,779,673 A | * | 7/1998 | Roth et al. ............. 604/101.03 |
| 5,800,392 A | | 9/1998 | Racchini ....................... 604/96 |
| 5,800,493 A | * | 9/1998 | Stevens et al. ............. 607/113 |
| 5,860,966 A | | 1/1999 | Tower ........................... 606/1 |
| 5,904,147 A | | 5/1999 | Conlan et al. ............. 128/899 |
| 5,951,497 A | * | 9/1999 | Wallace et al. ............. 600/587 |
| 5,980,485 A | | 11/1999 | Grantz et al. ................. 604/96 |
| 5,997,527 A | | 12/1999 | Gumucio et al. ........... 604/892 |
| 6,004,261 A | * | 12/1999 | Sinofsky et al. .............. 600/36 |
| 6,024,740 A | | 2/2000 | Lesh et al. .................... 606/34 |
| 6,139,570 A | * | 10/2000 | Saadat et al. ............... 607/105 |

FOREIGN PATENT DOCUMENTS

| | | |
|---|---|---|
| EP | 0299448 | 7/1988 |
| EP | 0311458 | 10/1988 |
| WO | 9737714 | 10/1997 |

* cited by examiner

*Primary Examiner*—Thomas Denion
*Assistant Examiner*—Ching Chang
(74) *Attorney, Agent, or Firm*—Thomas J. Engellenner; Lisa J. Michaud; Nutter McClennen & Fish LLP

(57) ABSTRACT

The present invention is directed to an anchoring balloon structure for use with catheters. The anchoring balloon structure contains an expandable balloon disposed about a port on a catheter, and a pressure-relief valve for regulating the pressure in the balloon and for providing irrigation to a body lumen. The pressure-relief valve is located external to the expandable balloon. The balloon, when filled with fluid, expands and is engaged in direct contact with the tissue. The increase in pressure caused by the balloon against the tissue causes any additional fluid to migrate into the valve region, whereby excess pressure is released and irrigation is provided to the body lumen.

24 Claims, 2 Drawing Sheets

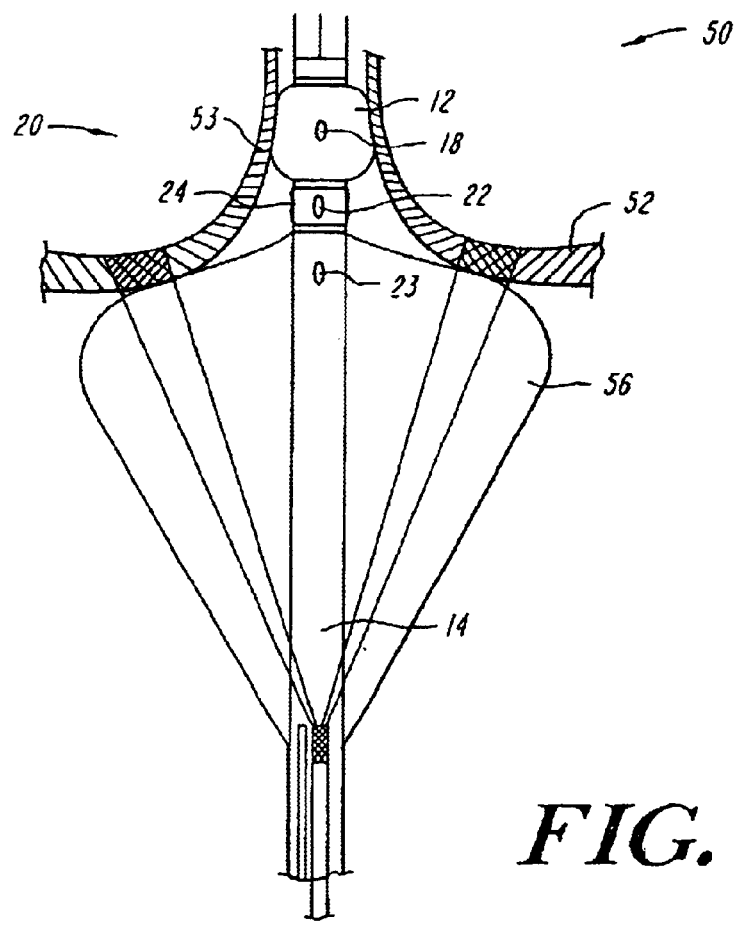
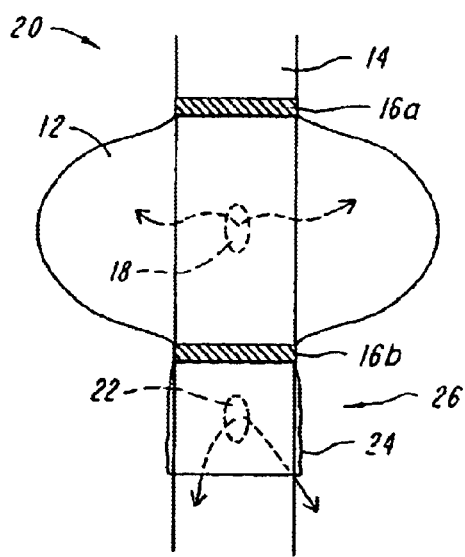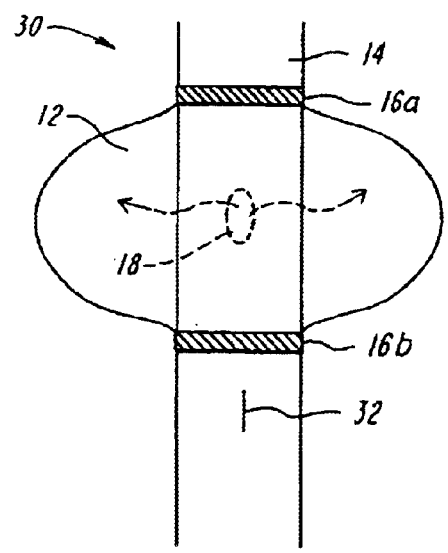
FIG. 1
FIG. 2
FIG. 3

CATHETER ANCHORING BALLOON STRUCTURE WITH IRRIGATION

BACKGROUND OF THE INVENTION

The present invention relates to balloon anchors for anchoring medical devices in a body lumen, and, in particular, to a balloon anchor for positioning a catheter or similar device within the heart.

Many abnormal medical conditions have resulted in disease and other aberrations along the lining or walls of a cavity or lumen within the body. Catheterization is a type of procedure performed for a wide variety of purposes, including vascular access for performing diagnostic, interventional, and therapeutic procedures. For example, cardiac catheters are inserted through blood vessels into a patient's heart to detect cardiac electrical signals, to apply electrical stimulation for diagnostic testing and to apply energy. Such energy can take the form of heat, electric current or radiation in order to eliminate (i.e. "ablate") the source of an arrhythmia. Other applications for ablation catheters include the treatment of tumors, such as breast or liver tumors, and the treatment of other aberrant biological structures. The catheter can also include other structures, such as a lumen through which chemical agents are delivered, mapping electrodes, and/or a sampling system for sampling a tissue or fluid specimen.

Current procedures include laparoscopic, endoluminal, perivisceral, endoscopic, thoracoscopic, intra-articular and hybrid approaches. Access into the body is made through a small incision. A catheter may be inserted at the incision into the cavity or working space and advanced through the lumen until it is positioned correctly. It is generally necessary to utilize a visualization technique of some sort in order to guide the catheter to a desired site of diagnosis and/or treatment and to ensure that the catheter remains at the desired location. Additionally, it is sometimes desirable or necessary to re-position the catheter at a particular location.

However, once the catheter is placed at the operative site, it is often desirable to fix the catheter at that position. Balloon structures are known in the art as mechanisms for anchoring a catheter in place. The balloon is inflated with fluid while the instrument is within the lumen. Once inflated, the balloon is engaged in direct contact with a wall of the lumen. The procedure is then performed. Once completed, the fluid is removed from the balloon, thereby deflating the balloon and allowing the catheter to be removed.

Although various designs of balloon anchored catheters have been quite useful, they often suffer from one or more limitations. In particular, it is difficult to know when an anchoring balloon is properly inflated. Because lumen dimensions will vary from one patient to another, it is sometimes impossible to predict how much fluid should be used to inflate the balloon. Under inflation of the balloon will result in a less than optimal anchorage of the instrument. On the other hand, over inflation of the balloon can damage the lumen. Moreover, when the balloon is large the wall tensions of the balloon are increased and there is a significant chance of balloon rupture. Additionally, balloons serve as total roadblocks to the passage of fluids, including but not limited to blood.

Consequently, there is a need for an anchoring balloon device that prevents over or under expansion of the balloon while providing irrigation to the lumen to locally reduce hematocrit and the chance of clotting.

SUMMARY OF THE INVENTION

The present invention is directed to an anchoring balloon structure for use with catheters. The anchoring balloon structure contains an expandable balloon disposed about a port on a catheter and a valve for regulating the pressure in the balloon while at the same time for providing irrigation to a body lumen. The balloon, when filled with fluid, expands and is engaged in direct contact with the tissue. Once the balloon is engaged, any additional inflation fluid will be released by the valve, thus regulating the pressure and also, optionally, providing irrigation at a treatment site (e.g. so that blood can be cleared from an ablation site). The balloon can be deflated by applying a vacuum which removes the fluid from the balloon. The valve prevents any back diffuision of external fluids thereby allowing the balloon to become ally deflated. Once fully deflated, the balloon can be easily removed from the body lumen.

In one embodiment, the valve is a pressure-relief valve connected to a second port in the catheter. The first and second ports are in communication with each other and with a single source of fluid. For example, a simple valve can be formed by surrounding the catheter body (and the second port) with an elastomeric sleeve. The sleeve covers the second port so as to force the fluid to enter the first port and fill the balloon. Once the balloon is full, the pressure of the balloon against the tissue is equal to or greater than the pressure of the sleeve over the second port. Any additional fluid is then forced into the second port and pushed out of the sleeve to irrigate the lumen.

In another embodiment, the pressure-relief valve comprises an elongated slit in the catheter. When the balloon is expanded, the pressure exerted on the expanded balloon causes the elongated slit to open and release fluid into the lumen. The pressure-relief valve can further comprise a fluid diff-using sleeve or a second expandable fluid diffusing balloon disposed over an elongated slit or a second port.

BRIEF DESCRIPTION OF THE DRAWINGS

The invention will be more fiully understood from the following detailed description taken in conjunction with the accompanying drawings, in which:

FIG. 1 is a schematic, cross-sectional view of a cardiac ablation apparatus having an anchoring balloon structure according to the invention.

FIG. 2 is a more detailed schematic, cross-sectional view of the anchoring balloon structure of FIG. 1.

FIG. 3 shows another anchoring balloon structure according to the invention having an elongated slit.

DETAILED DESCRIPTION

Figure 4:
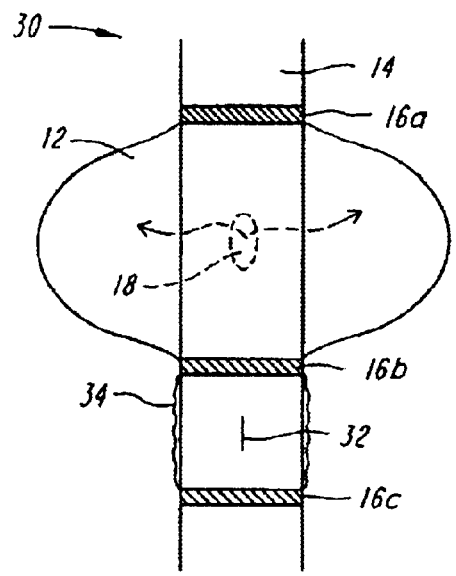
FIG. 4 shows another anchoring balloon structure according to the invention having an elongated slit and a permeable sleeve.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

In FIG. 1, a cardiac balloon catheter 50 is shown including an anchoring balloon structure 20. A primary balloon member 56 is disposed about the catheter 14 for inflation (via port 22) within the body (e.g. within the heart) to provide a transmission waveguide for projecting radiation of the tissue. The anchoring balloon structure 20 is shown engaged in direct contact with of a body lumen 52 (e.g. a pulmonary vein).

In FIG. 2 an anchoring balloon structure 20 is shown including a catheter 14 having a first port 18, an expandable balloon 12 disposed about the first port 18, and bonded collar elements 16A, 16B, disposed about each end of the expandable balloon element. A pressure-relief valve region 26 is shown. The anchoring balloon structure 20 is shown having first and second ports, 18, 22, which are in communication with a single source of fluid. An expandable balloon 12 is disposed about the first port 18 on the catheter 14. The expandable balloon is sealed to the catheter with bonded collars 16A and 16B. A sleeve 24 is shown disposed about the second port 22 on the catheter 14. The sleeve should impart a constriction about the catheter to insure that the sleeve will be retained in place. The durometer and tightness of the sleeve, as well as the size of the ports can be altered to impart the desired constriction about the catheter and regulate the effectiveness of the valve.

Figure 5:
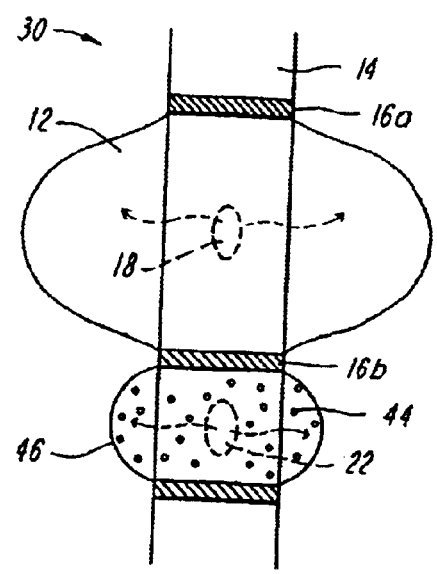
FIG. 5 shows another anchoring balloon structure according to the invention having a fluid diffusing balloon sleeve.

Another embodiment of an anchoring balloon structure 30 is shown in FIG. 3 having an elongated slit 32 in the catheter. In the presence of pressure on the expandable balloon, the fluid pushes through the slit, opening up a channel for delivery of the fluid to the body lumen. FIG. 4 shows an alternative embodiment of the anchoring balloon structure 30. A fluid diff-user sleeve 34 can be disposed about the elongated slit 32 in the catheter 14. FIG. 5 shows another alternative embodiment of the anchoring balloon structure 30 wherein a second, expandable, fluid diffusing balloon 46 can be disposed about the second port 22. The expandable balloon 46 can contain pores 44, which release fluid and provide irrigation.

In use, a conduit defined in the catheter 14 directs fluid into the expandable balloon 12. The pressure-relief valve 26 forces the fluid to enter the balloon thereby causing the balloon to expand. The balloon, when fully expanded, engages and is in direct contact with the tissue of the body lumen. The pressure exerted on the balloon is then equal to or greater than the pressure exerted by the pressure-relief valve. The pressure-relief valve is then forced to release any additional fluid thereby providing irrigation to the body lumen.

In the preferred embodiment, the sleeve prevents the fluid from entering the second port thereby causing it to exit the first port. Insertion of fluid into the balloon causes the balloon to expand until the pressure exceeds the pressure exerted by the pressure-relief valve. Initially, the pressure of the sleeve over the second port, the slit, or the expandable fluid diffusing balloon continues to prevent the fluid from exiting the second port. Once the balloon is engaged and in direct contact with the tissue of a body lumen, pressure is exerted on the balloon. Once the pressure on the balloon is equal to or great than the pressure of the sleeve over the second port, any additional pressure will force fluid to exit the second port and the sleeve. The excess pressure thus causes fluid to be pushed out of the proximal end of the sleeve. Since the proximal end of the sleeve is not in direct contact with the tissue, the risk of damage from jetting is prevented. Thus, irrigation is provided to the body lumen while regulating over or under expansion of the balloon.

The anchoring balloon structure can be deflated by applying a vacuum that removes the fluid from the balloon. A syringe or other known methods can be used to remove the fluid. The sleeve effectively seals the second port and prevents any back diffusion of external fluids, thereby allowing the balloon to become fully deflated. Once the anchoring balloon and primary balloon are fully deflated, the catheter can be easily removed from the body lumen.

The anchoring balloon structure can be a separate attachable, and in certain embodiments, detachable, portion which is located proximate to the distal end of a catheter. The balloon anchoring structure is fixedly attached or integrally locked into place on the distal end of a catheter by methods known in the art, e.g., gluing, melting, tying down, wrapping, ultrasonic welding, "snap on" fittings, male-female fittings, etc. Preferably the catheter end portion is energy transparent. An example of a catheter end portion is a silicone balloon anchor.

The materials used to construct the balloon anchor can be amorphous, semicrystalline, thermoplastics, or thermosets. Suitable materials include thermoplastic elastomers (TPE), latex, polyethylene terephthalate (PET), TPE blends, polyethylene, nylon, polyurethanes, silicone containing polymers, e.g., silastic, polyamides, poly(ether)arnides, fluorinated ethylene propylene (FEP), perfluoroalkoxy resin (PFA), polytetrafluoroethylene (PTFE), and ethylene-tetrafluoroethylene (ETFE).

The cardiac balloon catheter (shown in FIG. 1) can be used for a variety of procedures, including laparoscopic, endoluminal, perivisceral, endoscopic, thoracoscopic, intra-articular and hybrid approaches. For example, left ventricular fibrillation treatment can be performed by inserting the catheter 14 into the femoral artery. The catheter 14 is guided through the iliac artery, the aorta, through the aortic valve and adjacent to the wall of the left ventricle. Once the balloon 12 is proximate to the tissue ablation site, a solution can be injected through the lumen to expand and anchor the balloon. Excess fluid is released from the pressure-relief valve to force blood and/or body fluids away from the treatment site. An optical apparatus is then guided through the catheter 14 via a lumen to a position proximate to the tissue ablation site. Energy is emitted through the balloon 12 to ablate the tissue.

The term lumen, including derivatives thereof, is herein intended to mean any cavity or lumen within the body which is defined at least in part by a tissue wall. For example, cardiac chambers, the uterus, the regions of the gastrointestinal tract, the urinary tract, and the arterial or venous vessels are all considered illustrative examples of body spaces within the intended meaning.

What is claimed is:

1. An anchoring balloon device comprising:
   a flexible elongate member having an interior lumen extending therethrough for the delivery of an inflation fluid;
   an expandable balloon disposed about a portion of the flexible elongate member and in fluid communication with the lumen via at least one port, the balloon being adapted to be positioned at a treatment site; and
   a pressure-relief valve for regulating the pressure of fluid within the expandable balloon, the pressure-relief valve being configured to open and release irrigation fluid to the treatment site in response to excess pressure exerted on the expandable balloon.

2. A device according to claim 1, wherein the flexible elongate member is a catheter.

3. A device according to claim 1, wherein the pressure-relief valve provides irrigation.

4. A device according to claim 1, wherein the pressure-relief valve regulates pressure.

5. The device of claim 1, further comprising means for inflating the expandable balloon.

6. The device of claim 5, wherein the means for inflating the expandable balloon comprises a conduit defined in the interior lumen of the flexible elongate member for directing fluid into the expandable balloon.

7. A device according to claim 1, wherein the expandable balloon comprises a polymeric material.

8. A device according to claim 1, wherein the expandable balloon, when fully expanded, engages and is in direct contact with the tissue of a body lumen.

9. An anchoring balloon device comprising:
- a flexible elongate member having an interior lumen extending therethrough for the delivery of an inflation fluid;
- an expandable balloon adapted to be positioned at a treatment site and disposed about a portion of the flexible elongate member and in fluid communication with the lumen via at least one port; and
- a sleeve disposed about a second port in the flexible elongate member.

10. A device according to claim 9, wherein the sleeve provides irrigation.

11. An anchoring balloon device comprising:
- a flexible elongate member having an interior lumen extending therethrough for the delivery of an inflation fluid:
- an expandable balloon adapted to be positioned at a treatment site and disposed about a portion of the flexible elongate member and in fluid communication with the lumen via at least one port; and
- an expandable fluid diffusing balloon disposed about a second port in the flexible elongate member.

12. A device according to claim 11, wherein the fluid diffusing balloon provides irrigation.

13. An anchoring balloon device comprising:
- a flexible elongate member having a side wall and an interior lumen extending therethrough, the side wall having first and second ports in communication with a source of fluid;
- an expandable balloon disposed adapted to be positioned at a treatment site and about the first port of the flexible elongate member having a proximal end and a distal end, the expandable balloon being bonded at the proximal end and distal end to the flexible elongate member; and
- a sleeve disposed about the second port of the flexible elongate member.

14. A device according to claim 13, wherein the flexible elongate member is a catheter.

15. A device according to claim 13, wherein the sleeve provides irrigation.

16. A device according to claim 13, wherein the sleeve regulates pressure.

17. A device according to claim 13, further comprising means for inflating the expandable balloon.

18. A device according to claim 13, wherein the expandable balloon, when fully expanded, engages and is in direct contact with the tissue of a body lumen.

19. An anchoring balloon device comprising:
- a flexible elongate member having a side wall and an interior lumen extending therethrough, the side wall having a port in communication with a source of fluid;
- an expandable balloon adapted to be positioned at a treatment site and disposed about the port of the flexible elongate member having a proximal end and a distal end, the expandable balloon being bonded at the proximal end and distal end to the flexible elongate member; and
- an elongated slit passing through the flexible elongate member in communication with a source of fluid;
- wherein pressure exerted on the expandable balloon can cause the elongated slit to open and release fluid.

20. The anchoring balloon device of claim 19, further comprising a fluid diffuser sleeve disposed about the elongated slit.

21. A device according to claim 19, wherein the flexible elongate member is a catheter.

22. A device according to claim 19, wherein the elongated slit provides irrigation.

23. The anchoring balloon device according to claim 19, further comprising an expandable fluid diffusing balloon disposed about the elongated slit.

24. The anchoring balloon device according to claim 23, wherein the expandable fluid diffusing balloon provides irrigation.

* * * * *